(12) United States Patent
Cheng et al.

(10) Patent No.: US 8,974,529 B2
(45) Date of Patent: Mar. 10, 2015

(54) ARTIFICIAL DISC

(75) Inventors: Cheng-kung Cheng, Beijing (CN); Peng Chai, Beijing (CN); Fuqiang Zhao, Beijing (CN); Jianxiang Liu, Beijing (CN)

(73) Assignee: Beijing Naton Technology Group Co., Beijing (CN)

( * ) Notice: Subject to any disclaimer, the term of this patent is extended or adjusted under 35 U.S.C. 154(b) by 58 days.

(21) Appl. No.: 13/376,108

(22) PCT Filed: May 14, 2010

(86) PCT No.: PCT/CN2010/072787
§ 371 (c)(1),
(2), (4) Date: Dec. 2, 2011

(87) PCT Pub. No.: WO2010/139231
PCT Pub. Date: Dec. 9, 2010

(65) Prior Publication Data
US 2012/0095562 A1    Apr. 19, 2012

(30) Foreign Application Priority Data
Jun. 2, 2009    (CN) .......................... 2009 1 0085150

(51) Int. Cl.
*A61F 2/44* (2006.01)
*A61F 2/30* (2006.01)

(52) U.S. Cl.
CPC .......... *A61F 2/4425* (2013.01); *A61F 2002/302* (2013.01); *A61F 2002/30649* (2013.01); *A61F 2002/30841* (2013.01); *A61F 2230/0065* (2013.01); *A61F 2002/30062* (2013.01); *A61F 2002/30079* (2013.01); *A61F 2002/305* (2013.01); *A61F 2002/30502* (2013.01); *A61F 2002/30504* (2013.01); *A61F 2002/30505* (2013.01); *A61F 2002/30566* (2013.01); *A61F 2002/30604* (2013.01); *A61F 2002/30607* (2013.01); *A61F 2002/30647* (2013.01); *A61F 2002/30662* (2013.01)
USPC ...................................................... 623/17.14

(58) Field of Classification Search
USPC .......................................... 623/17.11–17.16
See application file for complete search history.

(56) References Cited

U.S. PATENT DOCUMENTS

| | | | |
|---|---|---|---|
| 2004/0148027 A1 * | 7/2004 | Errico et al. | 623/17.11 |
| 2006/0111783 A1 | 5/2006 | Aflatoon et al. | |
| 2006/0229724 A1 * | 10/2006 | Lechmann et al. | 623/17.11 |
| 2008/0161919 A1 * | 7/2008 | Melkent | 623/17.11 |

FOREIGN PATENT DOCUMENTS

| | | |
|---|---|---|
| CN | 1713866 A | 12/2005 |
| CN | 1819805 A | 8/2006 |
| CN | 101115450 A | 1/2008 |
| CN | 100400016 C | 7/2008 |
| CN | 101559003 A | 10/2009 |

OTHER PUBLICATIONS

International Search Report of PCT/CN2010/072787 dated Aug. 19, 2010.

* cited by examiner

*Primary Examiner* — David Bates
(74) *Attorney, Agent, or Firm* — Amster, Rothstein & Ebenstein LLP

(57) ABSTRACT

An artificial disc includes an upper joint (3) and a lower joint (7) which fit each other in a corresponding upper and lower relationship, and a removable fixed connection structure for fixedly connecting the upper joint (3) and the lower joint (7).

7 Claims, 2 Drawing Sheets

ARTIFICIAL DISC

TECHNICAL FIELD

The invention relates to the field of a prosthesis implants and, more particularly, to a intervertebral disc prosthesis.

BACKGROUND ART

An artificial disc replacement surgery is an effective way of treating degenerative disc diseases, and it gradually replaces the commonly-used spinal fusion surgery. The artificial disc replacement surgery has beneficial effects of restoring disc space height, decreasing stress concentration in adjacent segments, keeping a range of a joint motion (ROM) between adjacent vertebrals, preventing the degeneration of the zygapophyseal joint, and so on. The artificial disc replacement surgery uses a movable artificial disc as an implant to replace the natural disc and achieve moving function.

A common artificial disc mainly includes an upper joint and a lower joint which are fixedly connected to their adjacent segments (adjacent vertebral sub-endplate bone/adjacent vertebral bone), respectively. A ball-socket structure is disposed between the upper joint and the lower joint. The artificial discs are movable as soon as they are implanted into disc spaces, and thereby ensure achieving the beneficial effects above. However, since the upper and lower joints of the artificial disc are fastened to their adjacent segments mechanically at first, a period of time is needed to achieve stable combination between the upper and lower joints and their adjacent vertebral sub-endplate bones (such a stable combination is called biological fixation hereinbelow). Namely, the biological fixation is achieved by performing the mechanical fixation to embed a spike of the artificial disc into a vertebrae, and performing a surface processing to the artificial disc, so as to make sclerotin grow into the combination (contacting) surface of the artificial disc. Before the sclerotin grows into the combination surface of the artificial disc, the combination surfaces of the upper and lower joints of the artificial disc and the adjacent vertebral sub-endplate bones are unstable due to a relative movement between the upper joint and the lower joint. As a result, the combination between the upper and lower joints and the adjacent vertebral sub-endplate bones is delayed or fails at all. Therefore, clinical reports about the artificial discs currently on the market often show occurrence of a displacement or even a dislocation of the artificial disc, as well as a related submergence of the artificial disc.

SUMMARY OF THE INVENTION

The object of the present invention is to overcome the problem of the delayed combination or non-combination between the artificial disc and the adjacent vertebral sub-endplate bones after the artificial disc is implanted into the human body. For this, the invention provides an artificial disc and an assembling method thereof.

To achieve the object above, the main idea of the invention is to restrict several relative movements between the upper joint and the lower joint of the artificial disc before the sclerotin grows into the combination surface by a temporary fixed connection, thereby enhancing the stableness between the upper and lower joints and the adjacent vertebral sub-endplate bones.

According to a technical solution of the invention, a method for assembling an artificial disc is provided. The method comprises a step of fixing an upper joint and a lower joint of an artificial disc, which fit each other in an upper and lower relationship, on adjacent vertebral sub-endplate bones, respectively.

The method for assembling an artificial disc further comprises steps of: setting a fixed connection relation between the upper joint and the lower joint; and breaking the fixed connection relation between the upper joint and the lower joint after a biological fixation is achieved between the upper and lower joints and the adjacent vertebral sub-endplate bones.

The fixed connection relation restricts at least one of following movements: a movement of the upper joint relative to the lower joint or a movement of the lower joint relative to the upper joint, wherein a direction of the movement is vertical to an axis of a replaced disc; and a rotation of the upper and/or lower joint around its own rotating axis, wherein the rotating axis is a line passing through the joint and is parallel or coincident with the axis of the replaced disc.

The invention further provides an artificial disc comprising an upper joint and a lower joint which fit each other in an upper and lower relationship. And the artificial disc further comprises a removable fixed connection structure/removable intermediate structure for fixedly connecting the upper joint and the lower joint.

After the removable fixed connection structure has been fixedly connected the upper joint and the lower joint, at least one of following movements is restricted: a movement of the upper joint relative to the lower joint or a movement of the lower joint relative to the upper joint, wherein a direction of the movement is vertical to an axis of a replaced disc; and a rotation of the upper and/or lower joint(s) around its rotating axis, wherein the rotating axis is a line passing through the joint and is parallel or coincident with the axis of the replaced disc.

According to a more specific technical solution of the artificial disc of the invention, the upper joint and the lower joint fit each other by a ball-socket structure, and the removable fixed connection structure comprises: a ring-shaped member disposed between the upper joint and the lower joint, wherein the ring-shaped member has an inflatable structure, when the ring-shaped member is filled with gas or liquid, the ball-socket structure is disposed inside the ring-shaped member, and an upper end of the ring-shaped member abuts against the upper joint and a lower end of the ring-shaped member abuts against the lower joint, a friction force between the ring-shaped member and the upper joint and a friction force between the ring-shaped member and the lower joint restrict said movement, and the restriction to said movement is released after the gas or liquid is released from the ring-shaped member.

According to another specific technical solution of the artificial disc of the invention, the upper joint and the lower joint fit each other by a ball-socket structure, and the removable fixed connection structure comprises: a ring-shaped member disposed between the upper joint and the lower joint, wherein the ball-socket structure is disposed inside the ring-shaped member, and the ring-shaped member is movable along the axis of the replaced disc; when the ring-shaped member abuts against the upper joint, a friction force is generated between the ring-shaped member and the upper joint, and when a removable supporting member is disposed on the lower joint to support the ring-shaped member, said movement is restricted; and after the supporting member is released from the ring-shaped member, the restriction to said movement is released. Moreover, an end surface of the ring-shaped member contacting the upper joint adapts to an end surface of a corresponding end of the upper joint. The removable supporting member is a pin with a spring, wherein the spring is clamped by the pin and the lower joint, and an extending and retracting direction of the spring is parallel with an axis of the pin. As the spring extends, the pin extends and supports the ring-shaped member along a direction away from the lower joint, and the ring-shaped member is provided with recesses adapting to a contacting portion of the pin; as the spring is compressed to an extent, the pin retracts toward the lower joint, such that the support to the ring-shaped member is removed. The pin is made of magnetic material.

In another possible solution of the invention, the removable supporting member is a supporting member that fixedly supports the ring-shaped member, and the supporting member is made of degradable material.

The invention has the beneficial effects below.

There are some drawbacks in the prior art: in the period before the sclerotin grows into the combination surface (contacting surface) of the artificial disc, the movement of the artificial disc causes that the upper and lower joints cannot combine stably with the adjacent vertebral sub-endplate bones, thereby delaying the combination process between the upper and lower joints and the adjacent vertebral sub-endplate bones. Aimed at the drawbacks above, the method of the invention is mainly to fix the position relation between the upper joint and the lower joint so as to form an "integral joint" in the above period. Although the "integral joint" is also movable to produce an unstableness at the combination surfaces of the upper and lower joints and the adjacent vertebral sub-endplate bones, compared with the conventional unstableness at the combination surfaces of the adjacent vertebral sub-endplate bones caused by the upper and lower joints both having freedom there between, the "integral joint" can resist movement and make the forming of the biological fixation more stable, so the unstableness of the combination surfaces between the upper joint and the adjacent vertebral sub-endplate bone and between the lower joint and the adjacent vertebral sub-endplate bone is greatly reduced. As a result, a better mechanical environment is provided for sclerotin to grow into the combination surface of the artificial disc, so as to form a stable biological fixation. After the sclerotin grew into the combination surface of the artificial disc, the fixed connection between the upper joint and the lower joint can be removed to make the artificialdisc recover the desired movement function.

It can be learned from the above solutions, the artificial disc of the invention includes a temporary fixed connection structure for the upper and the lower joints base on the conventional artificial disc structure, thereby achieving the object of fixing the upper joint and the lower joint in the aforementioned growth stage of sclerotin. Moreover, in proper conditions (when the biological fixation is formed at the contacting surfaces between the upper and lower joints and the adjacent vertebral sub-endplate bones), the fixed connection structure can be removed to allow the upper joint and the lower joint to move relative to each other, and the artificial disc can recover its movement function.

BRIEF DESCRIPTION OF THE DRAWINGS

Hereinafter, the embodiments of the present invention will be described in detail with reference to the accompanying drawings, in which.

Throughout the drawings, the same component will be indicated by the same reference numeral, wherein.

"1" is used to indicate a combination surface; "2" is used to indicate a spike; "3" is used to indicate an upper joint; "4" is used to indicate a bulb; "5" is used to indicate a ring-shaped member; "6" is used to indicate a recess; "7" is used to indicate a lower joint; "8" is used to indicate a pinhole; "9" is used to indicate a pin; "10" is used to indicate a fastening ring; and "11" and "12" are used to indicate springs.

DETAILED DESCRIPTION OF THE PREFERRED EMBODIMENTS

A method for assembling an artificial disc will be described in detail according to embodiments of the invention hereinafter. However, it would be noted, the embodiments described here are intended only to illustrate, rather than to limit the scope of the invention.

Figure 1:
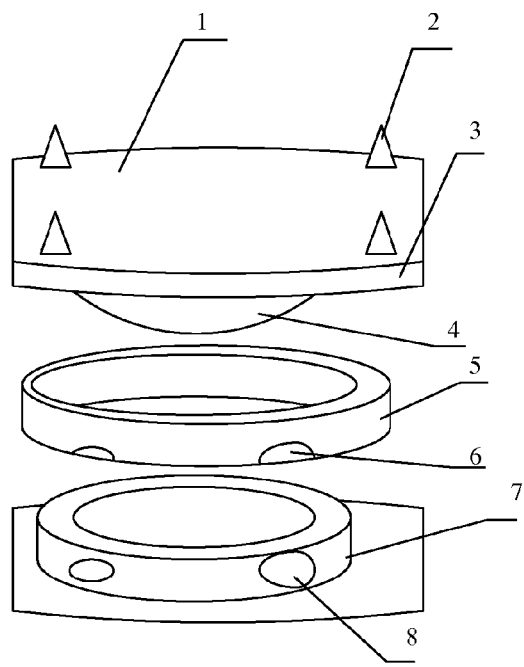
FIG. 1 is an exploded view showing positions of components in an artificial disc according to an embodiment of the invention.

An upper joint and a lower joint of an artificial disc are assembled in accordance with a preset fixed position relation (referring to positions of the upper and lower joints shown in FIG. 1), that is, the upper and lower joints are fixed to adjacent vertebral sub-endplate bones, respectively, via spikes 2. The adjacent vertebral sub-endplate bones will apply pressure to the upper and lower joints downwardly and upwardly, which is very beneficial to make a stable fixation between the artificial disc and the adjacent vertebraes, especially before the sclerotin grew into the combination surface (namely, before a biological fixation is formed).

After disposing the upper and lower joints by the above step, a fixed connection between the upper joint and the lower joint is formed. Such connection makes the upper joint and the lower joint restrict each other from moving. According to the above analysis, a main cause of the clinical problem in the prior art is the movement between the upper joint or the lower joint and the adjacent vertebral sub-endplate bones before the biological fixation is formed. The fixed connection can restrict the movements of the upper and lower joints, so as to ensure a preferable biological fixation between the upper and lower joints and the adjacent vertebral sub-endplate bones. There are many ways to form the fixed connection, and they are not illustrated herein for simplicity.

After the above steps, a connecting state between the upper and lower joints and the adjacent vertebral sub-endplate bones is detected. If the biological fixations between the upper and lower joints and the adjacent vertebral sub-endplate bones are achieved, the fixed connection can be removed via non-invasive surgeries or minimally invasive methods, and the artificial disc can recover its entire movement function.

Thus, the method for assembling the artificial disc according to the invention solves the problem of delayed combination or non-combination in the prior art.

Studies have shown that, at the period before the biological fixation is formed between the upper joint and the adjacent vertebral sub-endplate bone and between the lower joint and the adjacent vertebral sub-endplate bone, movements which seriously harm the biological fixation are mainly as follows: a movement of the upper joint relative to the lower joint or a movement of the lower joint relative to the upper joint, with a moving direction vertical to an axis of a replaced disc; and a rotation of the upper joint around its own rotating axis and/or a rotation of the lower joint around its own rotating axis (wherein the rotating axis is a line which passes through the joint and is parallel or coincident with the axis of the replaced disc).

The movements are illustrated below. The movement of the upper joint relative to the lower joint, or the movement of the lower joint relative to the upper joint, refers to a relative movement between the upper joint and the lower joint, particularly, a movement with a displacement component in a direction vertical to the axis of the replaced disc (the replaced disc refers to a disc replaced by the artificial disc). A human vertebral column has four curvatures (which are a cervical curvature, a thoracic curvature, a lumbar curvature and a sacral curvature). The moving direction of the above displacement component takes the axis (substantially a line) of the replaced disc as a reference. The movement of the upper joint relative to the lower joint or the movement of the lower joint relative to the upper joint can be decomposed into sub-displacements (displacement components) in two intersecting planes in a space, and if one of the above intersecting planes is set as a plane vertical to the axis of the replaced disc, and the movement of the upper joint or the lower joint can be decomposed to have a displacement component in this plane, the movement may seriously harm the formation of the biological fixation between the upper and lower joints and the adjacent vertebral endplates.

The following rotations may also seriously harm the formation of the biological fixation between the upper and lower joints and the adjacent vertebral endplates: the upper and/or the lower joint rotates around its own rotating axis which is a line passing through the joint and is parallel or coincident with the axis of the replaced disc. The axis referred herein is defined the same as the one referred in the above paragraph.

Consequently, in the method for assembling the artificial disc according to the invention, for achieving the fixed connection relation between the upper joint and the lower joint, at least one of the harmful movements should be restricted.

The technical solutions of the artificial disc according to the invention, which can perform the above method, will be described in detail by several examples with reference to the drawings.

FIG. 1 shows an artificial disc according to an embodiment of the invention. The artificial disc in this embodiment includes an upper joint 3 and a lower joint 7 which fit each other in an upper and lower relationship. The upper joint 3 and the lower joint 7 fit each other by a ball-socket structure. The ball-socket structure is a common movable connection structure, via which the upper joint 3 and the lower joint 7 can rotate relative to each other to achieve the movement function of a natural disc. The ball-socket structure includes at least two elements, a bulb 4 and a socket adapting to the bulb 4. A surface of the bulb 4 can slide relative to a surface of the socket, thereby achieving a rotating function of the bulb 4 relative to the socket. The bulb 4 is not limited to a standard ball, and it may also be an ellipsoid or the like. The ball-socket structure in the invention may be an assembly consisted of a bulb 4 which is fixed at the upper or lower joint and a socket which is correspondingly disposed at the lower or upper joint. Optionally, the ball-socket structure may also be an assembly consisted of two sockets which are disposed at both the upper and lower joints and an independent sphere as the bulb 4 which is disposed between the two sockets.

A removable fixed connection structure may be disposed between the upper joint and the lower joint. The removable fixed connection structure may fix the position relation of the upper joint and the lower joint, namely, the removable fixed connection structure may make the upper joint and the lower joint have no relative movement with each other. In the meantime, the fixed connection structure can be removed or detached, thereby removing the fixed connection relation between the upper joint and the lower joint. Since the relative movements between the upper joint and the lower joint are harmful to the biological fixation in different extents, the removable fixed connection structure can restrict the relative movements between the upper joint and the lower joint temporarily, which is of benefit to the object of the invention. Of course, the embodiment shown in FIG. 1 particularly restricts several movements which are most harmful to the biological fixation, so the embodiment is more effective to achieve the object of the invention. These movements are: the movement of the upper joint 3 relative to the lower joint 7, or the movement of the lower joint 7 relative to the upper joint 3, in such case, the moving direction is vertical to the axis of the replaced disc (that is, the lower joint 7 or the upper joint 3 moves approximately vertically); and the rotation of the upper joint 3 and/or the lower joint 7 around its own rotating axis, in such case, the rotating axis is a line passing through the joint and is parallel or coincident with the axis of the replaced disc. Said removable fixed connection structure allows the artificial disc to perform the method of the invention, in which several types of movements in a certain time period are restricted, and afterwards, the fixed connection structure can be removed to break the fixed connection relation between the upper joint 3 and the lower joint 7.

In the embodiment shown in FIG. 1, the removable fixed connection structure or intermediate structure may cooperate with the ball-socket structure for fitting the upper joint 3 and the lower joint 7 each other, and the ball-socket structure includes the bulb 4 disposed at the upper joint 3 and the corresponding socket disposed at the lower joint 7. Further, the removable fixed connection structure includes a ring-shaped member 5 disposed between the upper joint 3 and the lower joint 7. The ball-socket structure is disposed inside the ring-shaped member 5, and the ring-shaped member 5 can move along the axis of the replaced disc. Namely, the ring-shaped member 5 envelops the ball-socket structure and can move in a certain range (in the vertical direction in FIG. 1). Multiple pinholes 8 are arranged evenly in the lower joint 7 corresponding to the ring-shaped member 5, and pins for supporting the ring-shaped member 5 can be inserted into the pinholes 8. Two pinholes 8 shown in FIG. 1 are actually two ends of the pinholes running through the lower joint 7. Two pins are provided in FIG. 1 to provide a stable support to the ring-shaped member 5, and they are located at the front and the back of the lower joint in FIG. 1. The parts of the pins exposed from the pinholes 8 contact the ring-shaped members 5, so as to support the ring-shaped member 5. The parts of the ring-shaped member 5 which contact the pins are provided with recesses 6, so the pins not only support the ring-shaped member 5, but also restrict the rotation of the ring-shaped member 5. The pins are preferably positioned such that the ring-shaped member 5 is held by the pins and the upper joint 3 (in FIG. 1, the ring-shaped member 5 is held by both the pins and a flange of the upper joint 3), and a roughness of contacting surface between the ring-shaped member 5 and the upper joint 3 is increased, therefore, a relative large friction force can be generated between the ring-shaped member 5 and the upper joint 3. The friction force can restrict the movement of the upper joint 3 and the lower joint 7 relative to each other. Specifically, the friction force can restrict the movement which has a displacement component in the direction vertical to the axis of the replaced disc (namely, any direction in the plane parallel with the combination surface 1).

Since the ring-shaped member 5 is restricted from rotating along its own axis, and the upper joint 3 is also restricted by the ring-shaped member 5 from rotating along its own rotating axis (the rotating axis is a line passing through the joint and is parallel or coincident with the axis of the replaced disc), and there is also a fixed connection relation between the lower joint 7 and the upper joint 3, such that the lower joint 7 cannot rotate along its own rotating axis (the rotating axis is a line passing through the joint and is parallel or coincident with the axis of the replaced disc). With this, the embodiment shown in FIG. 1 can effectively restrict those movements most harmful to the biological fixation, and can prevent the problem of delayed combination or non-combination between the upper and lower joints and the adjacent vertebral sub-endplate bones in the prior art occurred during the early period of implantation of the artificial disc. After determining that the sclerotin of the human vertebrae has successfully combined with a contacting surface of the artificial disc (namely, the biological fixation is achieved) by clinical examinations or radiological examinations, the pins may be removed. Accordingly, the ring-shaped member 5 is dropped by the action of gravity, and does not contact the upper joint 3 any more, thereby the restriction to the rotation of the upper joint 3 is released, such that the artificial disc restore its movement function which it should have.

In another embodiment, the ring-shaped member 5, different from the one described above, has an inflatable structure which does not require pins and pinholes. Said inflatable structure refers to an airtight and hollow structure. When the ring-shaped member 5 is filled with gas or liquid, the ring-shaped member 5 expands and has the same structure shown in FIG. 1; and when gas or liquid in the ring-shaped member 5 is released, the ring-shaped member 5 compresses and is no more like the structure in FIG. 1. The ring-shaped member 5 is like a balloon. After the ring-shaped member 5 compresses, its volume is much smaller than the expanding one. In this embodiment, when the ring-shaped member 5 is filled with gas or liquid, its upper end abuts against the upper joint 3, and its lower end abuts against the lower joint 7 (i.e. abuts against the flanges of the upper joint and the lower joint, respectively). The contacting surfaces between the ring-shaped member and the upper and lower joints are disposed to have certain roughness, so as to make all the contacting surfaces between the ring-shaped member and the upper and lower joints generate friction forces which restrict the rotation of the ring-shaped member around the rotating axis passing through the ring-shaped member's own body, and also restrict the relative rotation between the upper joint 3 and the lower joint 7. The friction forces of the contacting surfaces between the ring-shaped member and the upper and lower joints also restrict the trend of the relative movement of the upper joint 3 and the lower joint 7 in the direction vertical to the axis of the replaced disc. With this, this embodiment can restrict several movements which are most harmful to achieve the biological fixation, and prevents the problem of delayed combination or non-combination occurred during the early period of implantation of the artificial disc. After determining that the sclerotin of the human vertebrae has been successfully combined with the contacting surface of the artificial disc (namely, the biological fixation is achieved) by clinical examinations or radiological examinations, the gas or liquid in the ring-shaped member 5 may be released, so as to release the restriction to the above mentioned movements, such that the artificial disc recovers its movement function which it should have.

Figure 2:
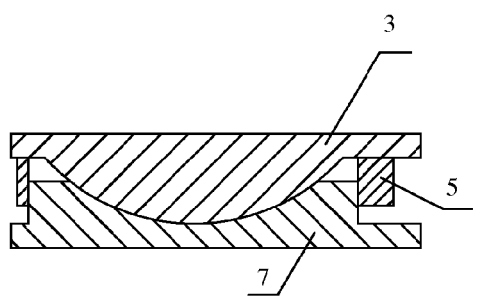
FIG. 2 is a sectional view of the assembled artificial disc according to the embodiment of the invention.

FIG. 2 shows the assembled structure of the artificial disc. It can be seen that a radial size of the ring-shaped member 5 is not uniform, and a wall of the ring-shaped member on the right side is thicker. In fact, the sectional view discloses such a technical feature: when the ball-socket joint formed by the upper and lower joints is not located right at the center of the artificial disc, it should be ensured that an end surface of the ring-shaped member 5 that contacts the upper joint 3 (namely, the upper surface of the ring-shaped member 5) has the proximate shape and area with the corresponding end surface of the upper joint 3 (namely, the lower surface of the flange of the upper joint 3) to the greatest extent (namely, the end surfaces are adapter to each other), thereby having an area as large as possible to support the upper joint 3. The larger area for supporting the upper joint 3 will bring the beneficial effect: the larger the combination surface 1 of the upper joint 3 contacts the adjacent vertebral sub-endplate bone, the faster the biological fixation process is achieved.

The pins and pinholes in FIG. 1 will be further illustrated by reference to FIGS. 3-6. Here, only several preferred embodiments will be provided, and a person skilled in the art may have various modifications according to the basic principles.

The pin in FIG. 1 should have functions of supporting the ring-shaped member 5, being removable or retractable from the pinhole 8 in order to remove the support to the ring-shaped member 5. The embodiments hereinbelow are designed aiming at the object.

Figure 3:
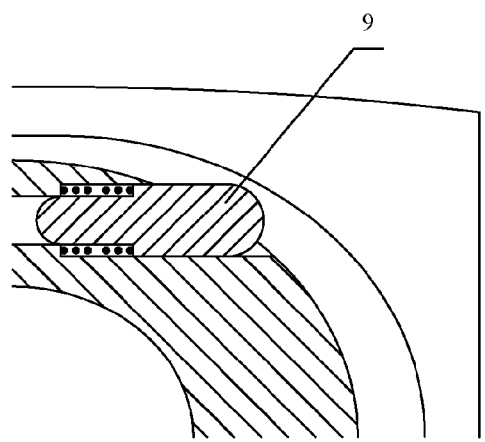
FIG. 3 is a sectional view showing a first example of a pin in the artificial disc according to the invention.

As shown in FIG. 3, the pillar-shaped pin 9 may be divided into two segments with different radial sizes, and the pinhole is a two-segment stepped hole composed of two coaxial holes with different diameters. The diameter of the small hole is slightly larger than the diameter of the small-sized segment of the pin 9, and smaller than that of the large-sized segment of the pin 9. The small-sized segment of the pin 9 is sleeved with a coil spring, whose axis is parallel or coaxial with that of the pin 9. The axial length of the spring in natural state is larger than the axial length of the small-sized segment of the pin 9, and one end of the spring abuts against a boundary (shoulder) between the two segments of the pin 9. The pin 9 disposed with the spring is inserted into the pinhole from the large-sized segment of the pinhole, and the other end of the spring abuts against the boundary of the two segments of the pinhole. When the spring is in a state of natural extension, a part of the pin 9 extends out of the pinhole from the end of the large-sized segment to support the ring-shaped member 5. When a force directing to left side in FIG. 3 is applied to the pin 9, the spring is compressed, and the pin 9 retracts into the pinhole, so the support to the ring-shaped member is removed. The force directing to left side in FIG. 3 may be provided by an external force pushing the pin 9 (such as in a minimally invasive surgery). Alternatively, the pin 9 may be made of magnetic material. In this case, if needed, a magnetic force may be applied to the pin 9 at left side in FIG. 3, such that the pin 9 retracts into the pinhole. After the magnetic force is removed, since the ring-shaped member is dropped off, the pin 9, no matter it is exposed out of the pinhole or not, will not affect the movement between the upper joint and the lower joint. The benefit effect of the solution using the magnetic material is, when the pin 9 is required to further retract into the pinhole, it is only needed to place a magnet outside the human body at a proper position without any wound cut on the human body, which may reduce the pain of the patient.

Figure 4:
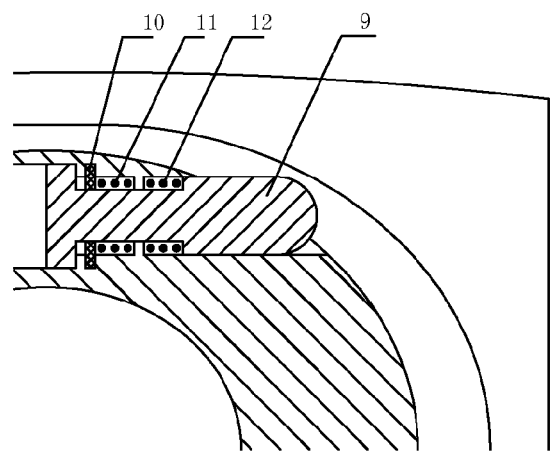
FIG. 4 is a sectional view showing a second example of the pin in the artificial disc according to the invention.

FIG. 4 shows another structure of the pin. The pin 9 is divided into three segments along its axis. The three segments have different radial sizes, that is, a large-sized segment, a middle-sized segment, and a small-sized segment, from left to right in radial size. The pinhole in FIG. 4 is also a two-segment stepped hole. The diameter of the large-sized segment of the stepped hole is approximate to the radial size of the large-sized segment of the pin 9, and the diameter of the small-sized segment of the stepped hole is approximate to the radial size of the middle-sized segment of the pin 9. The small-sized segment of the stepped hole is additionally provided with an inner rim, as shown in FIG. 4. The pin 9 is disposed in the pinhole, such that the large-sized segment of the pin 9 is disposed in the large-sized segment of the stepped hole (as shown in the left side of FIG. 4), and the middle-sized segment of the pin 9 is disposed in the small-sized segment of the stepped hole and is totally located on the right side of the inner rim. At the position the inner rim is located, the radial size (diameter) of the small-sized segment of the stepped hole is larger than the radial size of the small-sized segment of the pin 9 and smaller than the radial size of the middle-sized segment of the pin 9. A first coil spring 12 is disposed on the pin 9, and two ends of the first coil spring 12 abut against a right side of the inner rim and the boundary between the middle-sized segment and the small-sized segment of the pin 9, respectively. Additionally, a fastening ring 10 is embedded in an inner wall of the pinhole between the inner rim and the large-sized segment of the pin 9. Moreover, a second coil spring 11 is disposed on the pin 9, and two ends of the second coil spring 11 abut against a left side of the inner rim and the fastening ring 10, respectively. The fastening ring 10 is made of polyethylene material. The operating process of the pin 9 shown in FIG. 4 is as follows: initially, the second spring 11 between the inner rim and the fastening ring 10 is compressed, and the first spring 12 pushes the pin 9 to extend out of the small-sized segment of the pinhole so as to support the ring-shaped member; when the pin 9 is required to be retracted and moved back leftwards, the fastening ring 10 is melt by heating such as electromagnetic heating, such that the second spring 11 extends and then pushes the large-sized segment of the pin 9 to move leftwards. When the extending force of the second spring 11 is larger than the compressing force of the first spring 12, the pin 9 moves leftwards, and then the support of the pin 9 to the ring-shaped member is removed. Such a way of removing support only needs to perform an electromagnetic heating outside the human body, without any wound cut on the human body, thereby the pain of the patient can be reduced.

Figure 5:
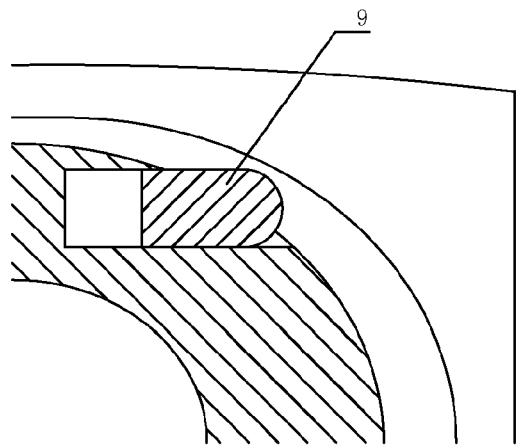
FIG. 5 is a sectional view showing a third example of the pin in the artificial disc according to the invention.

FIG. 5 shows such a technical solution of the pin: the pinhole is a blind hole, and an elastic member is disposed between the left side of the pin 9 with a diameter corresponding to the diameter of the pinhole and the bottom of the pinhole, thereby achieving the movement of the pin 9 in a left-to-right direction, that is, achieving a support function and a support removal function for the ring-shaped member. The elastic member may be controlled by a remote circuit, so the pin 9 can be remotely controlled outside the human body to retract (moving leftwards in FIG. 5) if necessary.

Figure 6:
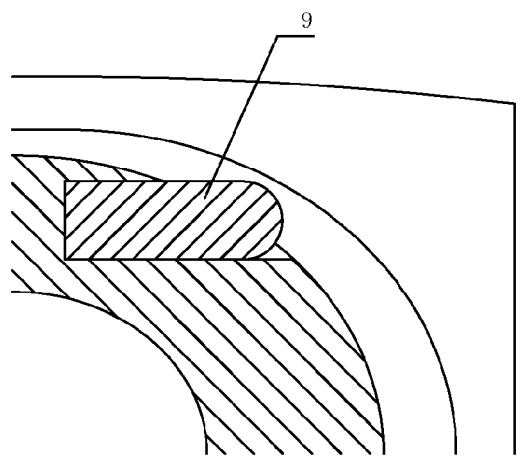
FIG. 6 is a sectional view showing a fourth example of the pin in the artificial disc according to the invention.

The pin 9 in FIG. 6 does not have a complex mechanical structure, and it is only an unmovable pin 9 in the pinhole. The pin 9 is made of degradable material, which may degrade gradually in the human body. The degradable material may be a synthetic polymer material such as PAL (poly lactic acid). The degradation process needs a certain period of time. After the pin 9 degrades to a certain extent, the pin 9 cannot support the ring-shaped member any more, and then the support is removed. During the degradation process, the pin 9 can still support the ring-shaped member, therefore, the time of degradation process may be designed to correspond to the time that the sclerotin grows into the combination surfaces of the upper joint and the lower joint, so as to achieve the object of the invention. The degradation time can be controlled by choosing a suitable degradable material and/or the size of the pin 9.

Although the invention has been described as above in reference to some typical embodiments, it is to be understood that the terms used therein are just illustrative and exemplary rather than restrictive. Since the invention can be applied in various forms without departing from the spirit or principle of the invention, it is to be understood that the abovementioned embodiments will not be limited to any specific details mentioned above, rather, they should be construed broadly in the spirit or concept of the invention defined by the appended claims. Therefore, the present invention aims to cover all the modifications or variations falling within the protection scope defined by the appended claims.

What is claimed is:

1. An artificial disc, comprising an upper joint and a lower joint which fit each other in an upper and lower relationship, wherein
 the artificial disc further comprises a removable intermediate structure for fixedly connecting the upper joint and the lower joint, and
 after a biological fixation is formed, the removable intermediate structure is configured to be removed, wherein
 the upper joint and the lower joint fit each other by a ball-socket structure, the removable intermediate structure comprises: a ring-shaped member disposed between the upper joint and the lower joint and having an inflatable structure, when the ring-shaped member is filled with a gas or liquid, the ball-socket structure is disposed inside the ring-shaped member, and an upper end of the ring-shaped member abuts against the upper joint and a lower end of the ring-shaped member abuts against the lower joint; a friction force between the ring-shaped member and the upper/lower joint restricts said movement; and the restriction to the movement is released after the gas or liquid is released from the ring-shaped member.

2. The artificial disc according to claim 1, wherein
 after the removable intermediate structure has been fixedly connected to the upper joint and the lower joint, at least one of following movements is restricted:
 a movement of the upper joint relative to the lower joint or a movement of the lower joint relative to the upper joint, wherein a direction of the movement is vertical to an axis of the replaced disc; and
 a rotation of the upper and/or lower joint around its own rotating axis, wherein the rotating axis is a line through the joint and is parallel or coincident with the axis of the replaced disc.

3. An artificial disc, comprising an upper joint and a lower joint which fit each other in an upper and lower relationship, wherein
 the artificial disc further comprises a removable intermediate structure for fixedly connecting the upper joint and the lower joint, and
 after a biological fixation is formed, the removable intermediate structure is configured to be removed, wherein
 the upper joint and the lower joint fit each other by a ball-socket structure, the removable intermediate structure comprises: a ring-shaped member disposed between the upper joint and the lower joint, wherein the ball-socket structure is disposed inside the ring-shaped member, and the ring-shaped member is movable along the axis of the replaced disc; when the ring-shaped member abuts against the upper joint, a friction force is generated between the ring-shaped member and the upper joint, and when a further removable supporting member is disposed on the lower joint to support the ring-shaped member, the movement is restricted; and after the removable supporting member is removed, the restriction to the movement is released, and the removable supporting member is a pin provided with a spring, wherein the spring is held by the pin and the lower joint, and an extending and retracting direction of the spring is parallel with the axis of the pin, when the spring extends, the pin supports the ring-shaped member along a direction away from the lower joint, and the ring-shaped member is provided with recesses adapting to a contacting portion of the pin; and when the spring is compressed to an extent, the pin retracts toward the lower joint, such that the support to the ring-shaped member is removed.

4. The artificial disc according to claim 3, wherein the pin is made of magnetic material.

5. The artificial disc according to claim 3, wherein the removable supporting member is a supporting member, which fixedly supports the ring-shaped member and is made of degradable material.

6. The artificial disc according to claim 3, wherein an end surface of the ring-shaped member that contacts the upper joint adapts to an end surface of a corresponding end of the upper joint, for achieving a largest area to support the upper joint.

7. An artificial disc, comprising an upper joint and a lower joint which fit each other in an upper and lower relationship, wherein the artificial disc further comprises a removable intermediate structure for fixedly connecting the upper joint and the lower joint, and after a biological fixation is formed, the removable intermediate structure is configured to be removed, wherein after the removable intermediate structure has been fixedly connected to the upper joint and the lower joint, at least one of following movements is restricted;

a movement of the upper joint relative to the lower joint or a movement of the lower joint relative to the upper joint, wherein a direction of the movement is vertical to an axis of the replaced disc; and a rotation of the upper and/or lower joint around its own rotating axis, wherein the rotating axis is a line through the joint and is parallel or coincident with the axis of the replaced disc, and wherein the upper joint and the lower joint fit each other by a ball-socket structure, the removable intermediate structure comprises: a ring-shaped member disposed between the upper joint and the lower joint and having an inflatable structure, when the ring-shaped member is filled with a gas or liquid, the ball-socket structure is disposed inside the ring-shaped member, and an upper end of the ring-shaped member abuts against the upper joint and a lower end of the ring-shaped member abuts against the lower joint; a friction force between the ring-shaped member and the upper/lower joint restricts said movement; and the restriction to the movement is released after the gas or liquid is released from the ring-shaped member.

* * * * *